United States Patent [19]

König et al.

[11] Patent Number: 4,625,052

[45] Date of Patent: * Nov. 25, 1986

[54] PROCESS FOR THE PRODUCTION OF POLYISOCYANATES WHICH HAVE A BIURET STRUCTURE

[75] Inventors: Klaus König, Leverkusen; Josef Pedain, Cologne; Helmut Woynar, Dormagen, all of Fed. Rep. of Germany

[73] Assignee: Bayer Aktiengesellschaft, Leverkusen, Fed. Rep. of Germany

[*] Notice: The portion of the term of this patent subsequent to Sep. 23, 2003 has been disclaimed.

[21] Appl. No.: 695,144

[22] Filed: Jan. 25, 1985

[30] Foreign Application Priority Data

Jan. 31, 1984 [DE] Fed. Rep. of Germany ........ 3403278

[51] Int. Cl.$^4$ ............................................. C07C 127/24
[52] U.S. Cl. ........................................ 560/335; 564/38
[58] Field of Search ..................... 564/38; 260/453 AB

[56] References Cited

U.S. PATENT DOCUMENTS

| | | |
|---|---|---|
| 3,124,605 | 3/1964 | Wagner ............................ 260/453 |
| 3,284,479 | 11/1966 | Windemuth et al. ............... 260/453 |
| 3,350,438 | 10/1967 | Hennig ............................. 260/453 |
| 3,367,956 | 2/1968 | Hennig et al. ..................... 260/453 |
| 3,441,588 | 4/1969 | Wagner et al. .................... 260/453 |
| 3,462,470 | 8/1969 | Emery et al. ...................... 260/453 |
| 3,526,652 | 9/1970 | Powers ............................. 260/453 |
| 3,824,266 | 7/1974 | Dietrich et al. ............. 260/453 AB |
| 3,862,973 | 1/1975 | Dietrich et al. ............. 260/453 AB |
| 3,896,154 | 7/1975 | Takahashi et al. ............ 260/453 P |
| 3,903,126 | 9/1975 | Woerner et al. ............. 260/453 AB |
| 3,954,825 | 5/1976 | Touhey, Jr. et al. ........ 260/453 AB |
| 3,976,622 | 8/1976 | Wagner et al. ............. 260/77.5 AT |
| 4,051,165 | 9/1977 | Wagner et al. ............. 260/453 AB |
| 4,147,714 | 4/1979 | Hetzel et al. ................ 260/453 AB |
| 4,176,132 | 11/1979 | Ide et al. ..................... 260/453 A |
| 4,192,936 | 3/1980 | Mohring et al. ...................... 528/59 |
| 4,218,390 | 8/1980 | Brusilovsky et al. ....... 260/453 AB |
| 4,264,519 | 4/1981 | Hennig et al. .............. 260/453 AB |
| 4,290,969 | 9/1981 | Komatsu et al. .............. 260/453 A |
| 4,292,255 | 9/1981 | Hennig et al. ............. 260/453 AR |
| 4,320,068 | 3/1982 | Schwindt et al. ........... 260/453 AB |
| 4,377,644 | 3/1983 | Kopp et al. ............................ 521/94 |
| 4,386,218 | 5/1983 | Rasshofer et al. ................... 564/38 |
| 4,525,590 | 6/1985 | Rasshofer et al. ................... 564/38 |
| 4,532,266 | 7/1985 | Rasshofer et al. ................... 564/38 |
| 4,532,317 | 7/1985 | Rasshofer ............................ 564/38 |

FOREIGN PATENT DOCUMENTS

| | | |
|---|---|---|
| 883504 | 6/1953 | Fed. Rep. of Germany . |
| 1570632 | 10/1973 | Fed. Rep. of Germany . |
| 140744 | 3/1980 | Fed. Rep. of Germany . |
| 889050 | 2/1962 | United Kingdom . |
| 1043672 | 9/1966 | United Kingdom . |
| 1044932 | 10/1966 | United Kingdom . |
| 3358010 | 12/1967 | United Kingdom ............... 260/453 |
| 1263609 | 2/1972 | United Kingdom . |
| 1460685 | 1/1977 | United Kingdom . |

OTHER PUBLICATIONS

"PUR–Anstrichostoffe"—Haputverhandes der deutschen gewerblichen Berufsgenossenschaft.
"Polyurethane Report"—Paintmakers Association of G.B. Ltd.
Angew, Chemie, 72, p. 1002.

Primary Examiner—Charles F. Warren
Assistant Examiner—R. A. Picard
Attorney, Agent, or Firm—Gene Harsh; Joseph C. Gil; Thomas W. Roy

[57] ABSTRACT

The present invention is directed to a process for the production of polyisocyanates which have a biuret structure by reacting aliphatic diisocyanates with water at elevated temperature, characterized in that the reaction is carried out in the presence of:

(a) $\alpha, \alpha, \alpha$-tri-substituted acetic acids, which do not have any further isocyanate-reactive group other than the carboxyl group, and/or (b) anhydrides of acids of the type mentioned in (a)

wherein up to 0.39 mols of component (a) are used per mol of water, up to about 2 mols of component (b) are used per mol of water, and the total quantity of components (a) and (b) is at least 0.02 to about 2 mols per mol of water.

8 Claims, No Drawings

PROCESS FOR THE PRODUCTION OF POLYISOCYANATES WHICH HAVE A BIURET STRUCTURE

BACKGROUND OF THE INVENTION

1. Field of the Invention

The present invention relates to an improved process for the production of polyisocyanates which have a biuret structure, excellent color quality and good monomer stability, by reacting aliphatic diisocyanates with water in the presence of specific carboxylic acids and/or the anhydrides thereof as catalysts.

2. Description of the Prior Art

Aliphatic polyisocyanates which have a biuret structure and in particular which are based on hexamethylene diisocyanate have achieved world-wide commercial importance for the production of light-fast lacquers which are extremely resistant to the effects of exposure and have as good a gloss-life as possible. Market demand for use in this field and in particular for clear and white-pigmented coatings, is for slightly colored or colorless products. Moreover, as small as possible a quantity of monomeric diisocyanates is required for safe processing, a quantity which does not increase even after a relatively long period of storage. Based on toxicological tests, safe processing is possible up to a maximum content of 0.7% of monomeric diisocyanate, as long as standard safety regulations are adhered to when processing the lacquer. The above-mentioned ceiling is found in the literature (e.g. Code of Practice "PUR-Paints" by the main association of the German commercial professional body and the "Polyurethane Report" by the Paintmakers' Association).

Over the years, a large number of processes have become known for producing polyisocyanates of this type, each of which suffers from specific problems and disadvantages and does not meet or meets only unsatisfactorily the above-mentioned demands on the product. The following processes are described by way of example:

Synthesis from diisocyanates and water, optionally in the presence of catalyst; c.f. DE-PS No. 1 110 394, DE-OS No. 1 668 377, DE-OS No. 2 308 015, GB-PS No. 889 050, GB-PS No. 1 399 228, DDR-PS No. 140 744.

Synthesis from diisocyanates and water in the presence of a solvent or a solvent mixture; c.f. DE-OS No. 2 808 801, DE-OS No. 3 030 655.

Synthesis from diisocyanates and water, the water being reacted in the form of vapor; c.f. DE-OS No. 2 918 739.

Synthesis from diisocyanates and hydrogen sulphide, optionally in the presence of catalyst; c.f. DE-AS No. 1 165 850.

Synthesis from diisocyanates and ammonia or ammonia-water mixtures, optionally in the presence of catalyst; c.f. DE-AS No. 1 227 003.

Synthesis from diisocyanates and amines: c.f. DE-PS No. 1 165 850, DE-PS No. 1 174 759, DE-OS No. 1 568 017, DE-OS No. 1 693 190, DE-OS No. 2 010 887, DE-OS No. 2 261 065, DE-AS No. 2 438 258, U.S. Pat. No. 3,824,266, DE-AS No. 2 609 995, DE-OS No. 2 803 103, DE-PS No. 883 504, GB-PS No. 1 263 609, c.f. also Angew. Chem. 72 P 1002.

Synthesis from diisocyanates and amine/alcohol mixtures; c.f. DE-OS No. 2 654 745.

Synthesis from diisocyanates and $\omega,\omega'$-diaminopolyethers; c.f. DE-OS No. 1 570 632, DE-AS No. 1 215 365.

Synthesis from diisocyanates and substituted ureas; c.f. DE-PS No. 1 101 394, DE-AS No. 1 227 004

Synthesis from diisocyanates and tertiary alcohols, optionally in the presence of catalysts; c.f. DE-AS No. 1 543 178, DE-AS No. 1 931 055, DE-OS No. 2 308 015.

Synthesis from diisocyanates and formic acid; c.f. DE-PS No. 1 174 760, DE-OS No. 2 308 015, DE-OS No. 2 437 130.

Synthesis from diisocyanates and aldoximes; c.f. DE-OS No. 3 007 679.

The known processes in which the diisocyanates are directly reacted with water are difficult to control on account of the non-homogeneity of the reaction mixture. This can lead to the formation of polyurea which dissolves with extreme difficulty. The dissolution of the polyurea necessitates the use of elevated temperatures over a long period of time, thereby impairing the color of the product. Even then, under certain circumstances, some of this polyurea remains undissolved as a precipitate which can only be filtered with difficulty and, thus, has to be separated by a costly operation before further processing. Furthermore, on account of the volatility of most diisocyanates, deposits of urea may form in the steam chamber of the reaction vessel. This is also the case in processes in which water is used in vapor form.

These deposits can only be avoided in hitherto known processes which use water as a biuretization agent if solvents or solvent mixtures are used to homogenize the reaction mixture. These processes, however, suffer from various disadvantages. On the one hand, large quantities of solvent are necessary which then have to be removed by distillation in a later stage of the process to produce the finished product and on the other hand, specific solvent mixtures of glycol ether acetates and phosphoric acid esters are required for colorless products. Furthermore, a reaction temperature of at least 140° C. is necessary in these processes to prevent the intermediate precipitation of insoluble ureas. If precipitates of this type are nevertheless formed, for example as a result of relatively low reaction temperatures, as in the processes in which water is used in the absence of solvent, a temperature of 160° C. and above is necessary to produce a clear product. This thereby leads to a more frequent occurrence of by-products and to a marked deterioration in the color quality.

Processes may be carried out in the absence of solvent by releasing water from a water-splitting compound during the reaction. The processes include in particular the commercially important process which uses tert.butanol and other tert. alcohols as biuretization agents. This process, however, also requires a temperature of about 180° C. involving all the above-mentioned disadvantages regarding the quality of the product. Furthermore, this process involves the loss of the biuretization agent with the release of combustible gases (isobutene).

The reaction of diisocyanates with aldoximes is also characterized by the loss of the biuretization agent which is difficult to obtain and the production of easily-volatile by-products (nitriles) which cannot be re-used.

Reacting diisocyanates with hydrogen sulphide produces the toxic, low-boiling carbon oxysulphide which cannot be re-introduced into the process and has to be removed by a costly operation.

All the above-mentioned processes share the common factor that some of the diisocyanate is converted into amines, that is the precursor of the isocyanates, by reaction with the biuretization agent. For this reason, processes were proposed in which diisocyanates are reacted directly with the diamine-precursors thereof to produce the biuret-polyisocyanates. However, in paricular in the case of the most important substituent from a commercial point of view, 1,6-diisocyanatohexane, and even when highly-developed mixing processes are used, polyureas are produced which only dissolve with difficulty on account of the high reactivity of the diamines. The dissolution of the polyureas requires extremely high temperatures and this is accompanied by the deterioration in the color quality and an increased frequency of by-products. Carbodiimides and the secondary products of carbodiimides are produced in addition to dimeric uretdiones and trimeric isocyanurates. The carbodiimides have an adverse effect on the monomer stability of the end product.

The tendency to form polyureas which only dissolve with difficulty may be reduced by using diamines whose carbon frame does not correspond to the diisocyanates which are used and whose reactivity may be markedly reduced in a suitable manner, for example by steric hindrance. The products contain, among other things, a large quantity of monomeric diisocyanates which are produced from the diamine reactants and which cannot be reduced by thin-layer distillation.

If $\omega,\omega'$-diaminopolyethers are used, liquid, biuret-containing polyisocyanates are obtained; this solution is, however, costly, on account of the additional synthesis of the biuretization agent. Moreover, the ether groups which are present in these products cause the lacquer products which are produced therefrom to have poor behavior under the effects of exposure.

The formation of polyureas may be prevented by using monoamines or N,N'-disubstituted ureas. In this case, however, the volatile monoisocyanates which result from these biuretization agents have to be removed from the reaction mixture. This is only partially possible, even at elevated temperature, because of the chemical equilibriums of the reactions which take place.

Products which have good color quality may be produced by carefully reacting diisocyanates with formic acid, but these products still contain a large quantity of N-formyl groups. To produce a polyisocyanate with an essentially biuret structure, a reaction temperature of greater than 160° C. is required over a relatively long period of time and this produces a marked yellowing of the products. The biuretization agent is moreover consumed with the release of toxic carbon monoxide, thereby causing considerable problems when compared to processes which were also proposed in which ammonia and amine-alcohol mixtures respectively are used. Apart from other disadvantages, processes of this latter type produce products which have a modified structure and a different property spectrum. This holds true for products which are produced by reacting diisocyanates with ammonia.

It has now been found that polyisocyanates which have a biuret structure, outstanding color quality and good monomer stability may be produced by reacting an excess of aliphatic diisocyanates with water in the presence of specific tri-substituted acetic acids or anhydrides of the said carboxylic acids.

SUMMARY OF THE INVENTION

The present invention is directed to a process for the production of polyisocyanates which have a biuret structure by reacting aliphatic diisocyanates with water at elevated temperature, characterized in that the reaction is carried out in the presence of:

(a) $\alpha,\alpha,\alpha$-tri-substituted acetic acids, which do not have any further isocyanate-reactive group other than the carboxyl group, and/or (b) anhydrides of acids of the type mentioned in (a) wherein up to 0.39 mols of component (a) are used per mol of water, up to about 2 mols of component (b) are used per mol of water, and the total quantity of components (a) and (b) is at least 0.02 to about 2 mols per mol of water.

DETAILED DESCRIPTION OF THE INVENTION

Linear or branched aliphatic diisocyanates having from 4-30 and preferably from 5-12 carbon atoms in the hydrocarbon radical which may also have one or more ester groups, are used in the process according to the present invention. The following are given by way of example: 1,4-diisocyanato-butane, 1,5-diisocyanato-pentane, 1,6-diisocyanato-hexane, 1,8-diisocyanato-octane, 1,10-diisocyanato-decane, an isomer mixture of 2,2,4-trimethyl-1,6-diisocyanatohexane and 2,4,4-trimethyl-1,6-diisocyanatohexane, 2-methyl-1,5-diiso-cyanato-pentane, 2,2-dimethyl-diisocyanato-pentane, $\omega$-isocyanato-caproic acid (2-isocyanatoethyl)-ester and $\alpha,\omega$-diisocyanato-caproic acid ethyl esters.

1,6-diisocyanatohexane is most preferably used in the present process. Standard quality diisocyanates may be used so that preliminary purification or heat treatments are not necessary.

The additives which are essential to the present invention are (a) $\alpha,\alpha,\alpha$-tri-substituted acetic acids, which do not have any isocyanate-reactive group other than the carboxyl group and the $\alpha$-carbon atom of which is not linked to hydrogen, as it is tri-substituted;

and/or (b) anhydrides of acids of this type.

Suitable tri-substituted acetic acids and acetic acid anhydrides respectively are, for example, compounds corresponding to the general formulae

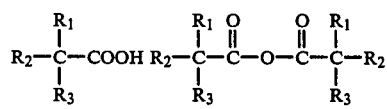

wherein $R_1$, $R_2$ and $R_3$ represent the same or different radicals and represent alkyl, alkoxy or alkoxyalkyl groups or wherein two of the substituents along with the carbon atom of the acetic acid and the acetic acid anhydride respectively in the $\alpha$-position may form a cycloaliphatic ring.

Preferred compounds of the above-mentioned formulae are compounds, in which the radicals $R_1$, $R_2$ and $R_3$ represent alkyl radicals and in which the sum of the carbon atoms of the radicals $R_1$, $R_2$ and $R_3$ is from 3-6 and preferably 3 or 4 and in particular 3. 2,2,2-trimethyl acetic acid (pivalic acid), 2,2-dimethyl butyric acid, 2,2,3-trimethyl butyric acid, 2-methyl-2-methoxymethyl-propionic acid or 1-methylcyclopropane carboxylic acid are, for example, suitable. Methacrylic acid is also a suitable tri-substituted acetic acid according to the present invention since it fulfills the above-mentioned condition that the α-carbon atom is not bound to any hydrogen atom. As explained, the corresponding acid anhydrides may be used instead of or combined with previously mentioned tri-substituted acetic acids.

Trimethyl acetic acid and/or trimethyl acetic acid anhydride is preferably used. It is also possible in principle to use a suitable tri-substituted acetic acid together with an anhydride of another suitable tri-substituted acetic acid.

In the process according to the present invention, the quantity of water, tri-substituted acetic acid and/or the anhydride thereof is calculated in such a way that the following requirements are met:

1. The mol ratio of starting diisocyanate to "total water" is from about 3:1 to 20:1 and preferably from about 5:1 to 12:1. The term "total water" is to be understood, in this instance, as not only designating the water which is added in substance as a biuretization agent, but also the potential water which is introduced in the form of acid and is formed when the acid is completely converted into its anhydride with the splitting off of water. The term "one mol of (potential) water" corresponds to the term "two mols of tri-substituted acetic acid".

2. The tri-substituted acetic acids and/or the anhydrides thereof are, moreover, used in a quantity such that up to 0.39 and preferably up to about 0.25 mols of tri-substituted acetic acid and/or up to about 2 and preferably up to about 0.5 mols of anhydride of a tri-substituted acetic acid are allotted to each mol of water, on condition that the total quantity of tri-substituted acetic acid and/or anhydride of a tri-substituted acetic acid is at least about 0.02 mols, preferably at least about 0.03 mols, and at most 2 mols, preferably at most about 0.5 mols, per mol of water.

It may be effective to carry out the present process in the presence of a solvent which is inert to isocyanates and acid and to a certain extent water-miscible.

The following are examples of solvents which may be used: ethers such as diisopropylether, ethylene glycol dimethylether, diethylene glycol dimethylether, 1,4-dioxane, tetrahydrofuran and 1,2-dimethoxypropane; esters such as butyrolactone, ethylene glycol carbonate and propylene glycol carbonate; ethyl esters such as methoxyethylacetate, ethoxyethylacetate, 1-methoxypropyl-2-acetate, 2-methoxypropyl-1-acetate, 1-ethoxypropyl-2-acetate and 2-ethoxypropyl-1-acetate; ketones such as acetone and methylethylketone; nitriles such as acetonitrile, propionitrile and methoxypropionitrile; sulphones such as sulpholane, dimethylsulphone and diethylsulphone: and phosphoric acid esters such as trimethylphosphate and triethylphosphate.

The following are solvents which are less preferred: tetramethylurea, N-methylpyrrolidone, dimethylformamide and dimethylacetamide.

The present process is carried out at a temperature of about 50°–160° C. and preferably about 80°–140° C.

The process is conventionally carried out under ambient pressure. The process may, of course, also be carried out under a pressure of about 1 to 50 bars and preferably about 1 to 5 bars particularly if low-boiling solvents are used.

When biuret polyisocyanates are produced by using water as a biuretization agent, the latter reacts with diisocyanates with the intermediate formation of carbamic acid to produce the corresponding amines and carbon dioxide. The amines which are formed react with further isocyanate in an extremely rapid reaction to produce ureas which dissolve with difficulty and which subsequently react with excess isocyanate to produce the end product.

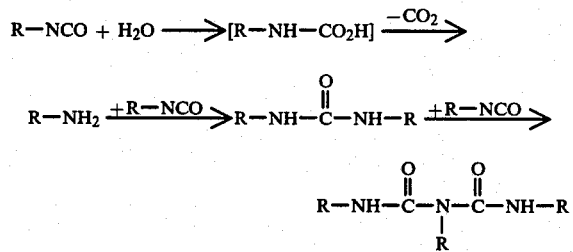

As already explained, only with difficulty, at great expense and with the acceptance of the disadvantages can this reaction sequence produce products which have an acceptable color quality and an acceptable quantity of by-products. The main reason for the discoloration and production of by-products which impair the stability of the monomers is the high temperature to which the product has to be subjected in all the hitherto known processes.

If carboxylic acids are reacted with isocyanates, then (as in the above-described primary reaction with water) an unstable, mixed carbamic acid carboxylic acid anhydride is obtained which, as in the water-reaction also decomposes to form a carboxylic acid amide with the splitting off of carbon dioxide. This reaction method (I) is conventionally described in the literature for reacting aliphatic isocyanates with carboxylic acids.

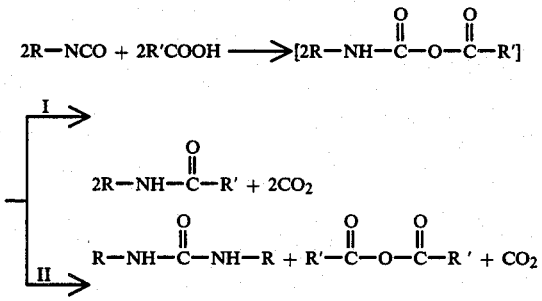

Occasionally and in particular for aromatic isocyanates an alternative reaction method (II) is mentioned, which results in the formation of urea, carboxylic acid anhydride and only half the quantity of carbon dioxide.

DE-AS No. 1 174 760 describes that when formic acid is reacted with isocyanates, only urea is formed with the splitting off of carbon monoxide as an inner anhydride and the resulting ureas are subsequently reacted with further isocyanate to produce biurets. Several subsequent works and the teaching of DE-OS No. 2 437 130 show that very large quantities of N-formylurea groups are contained in the products according to DE-AS No. 1 174 760 instead of biuret groups.

The finding according to the present invention is that the reaction of diisocyanates and water to produce ureas and in particular also the subsequent reaction of the resulting ureas to produce biurets in the presence of the carboxylic acids and/or the anhydrides thereof which are essential to the present invention is carried out much quicker and at a lower temperature.

Biuret polyisocyanates may be produced according to the present invention at a temperature as low as about 80° to about 120° C. without the ureas which are intermediately formed concentrating and precipitating, but instead rapidly reacting to form biurets. In the absence of the acids and/or anhydrides which are essential to the present invention, the reaction of, for example, 1,6-diisocyanatohexane with water at a temperature below 140° C. even in the presence of much hydrophilic solvent leads to the precipitation of the intermediately formed ureas. Homogenization by the formation of biuret requires a relatively long treatment at elevated temperature, for example 2 hours at 180° C.

The acids and anhydrides respectively according to the present invention obviously act as carriers in that a mixed anhydride is formed from the acid (which is either added as such or produced from anhydrides and water by hydrolysis when anhydrides are used) and the diisocyanate. The mixed anhydride either reacts with water to form carbamic acid and carboxylic acid or in particular with the urea which is already present to form biuret and carboxylic acid. For this reason it is no longer necessary to use a large quantity of solvent to produce a completely homogeneous reaction mixture. If, on the contrary, 1,6-diisocyanatohexane is directly reacted with water in the absence of or in the presence of a small quantity of solvent and in the absence of the catalysts according to the present invention, polyureas are obtained which are extremely difficult to dissolve. As discussed, the dissolution of the polyureas requires elevated temperatures over a long period of time.

Acids other than those essential to the present invention, such as formic acid or acetic acid, do not have the above-mentioned effect or have it only to a limited extent since they form acid amides to a large extent from which the free acids cannot be reformed. If formic acid is used, the partial formation of ureas and biurets respectively is observed. The quantity of acid which reacts in this manner is converted, however, into the inner anhydride (carbon monoxide) which under the reaction conditions does not reproduce formic acid by hydrolysis.

The present invention may be carried out for example, in the following manner:

The diisocyanate which is used is introduced into a mixing reactor. The mixing reactor at a temperature of about 60° to 140° C. preferably about 80° to 120° C., is optionally provided with a measuring device for the resulting carbon dioxide together with some or all of the solvent which may be used.

Water, the acid and/or the anhydride thereof which are used according to the present invention either together or separately, optionally together with a solvent are metered into the diisocyanate or the diisocyanate-solvent mixture.

If anhydrides are used, they are advantageously introduced together with the diisocyanate and optionally a solvent; whereas, when acids are used, the incremental metering of acid and water is preferred.

If, for example, pivalic acid is used, the reaction is advantageously carried out at a temperature of about 80° to 100° C. In this instance, pivalic acid and water may be metered together in admixture with a solvent, the quantity of solvent being calculated such that a homogeneous mixture is produced. The remaining quantity of solvent may then be introduced together with the diisocyanate into the reaction vessel.

If the acid anhydride, which is produced during the reaction or is continually present in the reaction mixture, is subsequently separated and hydrolyzed to reproduce acids, a solvent is advantageously used which has a boiling point between the boiling points of diisocyanate and acid anhydride. For example, if 1,6-diisocyanatohexane is used, solvents which meet this requirement are triethylene glycol dimethylether, diethylene glycol monoethylether acetate and phosphoric acid triethylester. During disstillation, the pivalic acid anhydride may be completely removed from the reaction mixture with some of the solvent and hydrolyzed, without further purification, to produce acid.

The boiling point of the solvent to be used is, in contrast, unimportant if carboxylic acid anhydrides are used as, in this instance, the anhydride may be introduced together with the diisocyanate and on completion of the reaction may be separated from the biuret-polyisocyanate together with excess monomeric diisocyanate and reused without having to be reprocessed.

In either case the quantity of solvent is substantially less than the quantity used, for example, in the process according to the teaching of DE-OS No. 2 808 801. In this process the quantity of solvent had to be about half the quantity of isocyanate so that a homogeneous reaction mixture would be obtained. In the process according to the present invention, in contrast, from ⅓ to 1/10 of the above-mentioned quantity suffices, thereby markedly reducing the cost of distillation.

If the reaction is catalyzed by the anhydrides of acids instead of by the acids themselves, about double the molar quantity of anhydride is necessary to achieve comparable reaction times and temperatures. For this reason it is advantageous in a reaction which is catalyzed other than by acids to work at slightly increased temperatures of from about 100°-120° C. to reduce the quantity of anhydride which is required for satisfactory reaction speed. If the same quantity of anhydride as acid is to be used, a reaction temperature of about 120° C. has to be chosen to achieve the same reaction speed as in the acid-catalyzed reaction.

Of course, the acid-catalyzed reactions may also be carried out at a higher temperature; however, an increase in temperature does not constitute an advantage, but impairs, albeit only slightly, the quality of the products by producing by-products and in particular by producing dimeric isocyanates (uretdiones).

A method is also possible, according to which diisocyanate, acid and/or anhydride, water and optionally solvent are introduced together at a low temperature and the reaction is started by heating the mixture. If acid is used as a catalyst, the reaction begins at about 50°-60° C. and if anhydrides are used as catalysts, a slightly higher temperature (about 80° C.) is required. Intermediate urea precipitates are inevitably produced which require relatively high temperatures and long periods of time for dissolution and formation of biuret. Therefore, this method is less preferred.

If low boiling solvents (which are advantageously used, in particular in anhydride-catalyzed processes) are used, then it may be effective to work under excess pressure to reduce losses of solvent or water. The maximum pressure during the reaction is advantageously limited to 6 bars by appropriate steps, such as by a pressure valve, because at this pressure or less, it is possible to use conventional technical apparatus without difficulty. The reaction may, of course, also be carried out under relatively high pressures, such as under the full pressure of the carbon dioxide which is produced during the reaction. Depending on the temperature and level to which the reactor is filled, a pressure of up to at most 20 bars may be produced. However, in cases of this type specific high pressure apparatus are required.

The ratio of NCO-groups to water and optionally acid, may vary within broad limits, as already explained. The ratio determines the oligomer distribution of the resulting biuret-polyisocyanate and this determines the properties of the product such as isocyanate content and viscosity. Thus, two biuret-polyisocyanates having viscosities of 10,000 and 2,500 mPa.s at 23° C. may be achieved, according to the present invention if 3/11 and 1/6 respectively of the NCO groups which are used are reacted according to the present process with acid or acid/water mixture, to produce biurets.

End products which have an even smaller viscosity may, of course, be produced by using larger excesses of starting diisocyanate. The process is, however, increasingly uneconomical on account of the increased cost of distillation and the smaller volume/time yield.

On the other hand, the range of variation is limited by the formation of products which have an extremely high viscosity, and which become increasingly incompatible with the non-polar solvents used for processing polyisocyanates. If more than half the NCO-groups of the diisocyanate which was originally present (mol ratio of diisocyanate: "total water"<3:1) are reacted, the formation of insoluble gels has, of course, to be reckoned with.

After termination of the reaction excess diisocyanate, carboxylic acid anhydride and any solvents present are removed from the reaction mixture by distillation. If no solvent was used and the acid anhydride formed has a lower boiling point than the diisocyanate, it is advantageous first to remove most of the acid anhydride from the reaction mixture by distillation under vacuum. In practice, about 90% of the anhydride present in the reaction mixture may effortlessly be isolated in pure form, free from diisocyanate. The residual anhydride remains in the reaction mixture and is separated from the biuret polyisocyanate in a subsequent thin-layer distillation operation together with the excess diisocyanate. Since the anhydride which remains in the excess diisocyanate is not detrimental to the present process, the resulting mixture may be reused without further processing. The anhydride which has been previously separated may be hydrolyzed to produce acid simply by heating it with water and may also be reused. A complete hydrolysis of the resulting anhydride is unnecessary as the remaining anhydride also has a catalytic effect.

The method of completely removing acid anhydride which has formed by distillation from the reaction solution produces a product which contains diisocyanate as an impurity, and if it is to be hydrolyzed to produce acid for the purpose of reuse, it has to be purified in a further distillation stage. Thus, it is advantageous when relatively small quantities are used to collect the anhydride which has been produced from various mixtures and process it together.

If the anhydride of the carboxylic acid which is used has a higher boiling point than the diisocyanate which is used, both are removed together by thin-layer distillation. However, a large quantity of the diisocyanate has to be removed on account of the higher excess of isocyanate and by-products are increasingly produced which are concentrated in the end-product during removal of this excess diisocyanate.

If acid anhydride is used as a catalyst, this may be removed by distillation and preferably by thin-layer evaporation, together with excess diisocyanate and solvent which may be present. The resulting distillate may be reused without further purification, while compensating for minimal losses by the addition of a corresponding quantity of anhydride or more advantageously acid.

If, however, the anhydride (after hydrolysis) is to be reused in the form of a free acid, it is advantageous to remove by distillation the diisocyanate, carboxylic acid, anhydride and solvent which may be present in the reaction mixture. If no solvent is used, it is advantageous to extract the acid anhydride as completely as possible from the mixture which has formed by distillation under vacuum if it has a lower boiling point than the diisocyanate which is used. In practice it is justifiable from an economical point of view to initially distill off a portion of anhydride in pure form until the mixture contains 1–3 weight % anhydride based on the weight of the diisocyanate. The remaining anhydride remains in the reaction mixture and is subsequently removed by thin-layer distillation together with the excess starting diisocyanate. Since the anhydride which remains in the excess diisocyanate does not disturb the reuse of the diisocyanate for the process of the invention the resulting mixture which is distilled off by thin-layer distillation may be reused in the process. The main portion of the anhydride which has been distilled off may be hydrolyzed with water to form the acid which may also be used again. A complete hydrolysis of the anhydride is not necessary because the remaining anhydride also has a catalytic effect.

The method of removing the anhydride which has been formed completely from the reaction mixture yields an anhydride which still contains some traces of diisocyanate and has, therefore to be purified by further distillation before it is hydrolyzed to form the acid.

If the anhydride corresponding to the carbonic acid which has been used has a higher boiling point than the starting diisocyanate both are simultaneously removed by thin-film distillation with subsequent separation of the distillate by another distillation if the anhydride is to be hydrolyzed to form the acid. Since in such case small amounts of anhydrides always remain in the product of the process i.e. in the biuret isocyanate this method is not preferred at all. This means that the acids which are used in the process of the invention yield preferably anhydrides which have a lower boiling point than the starting diisocyanate.

If a solvent is also used, depending on the boiling point, it may be separately removed from the reaction mixture, removed together with the anhydride or removed together with the excess diisocyanate and reintroduced into the process. If the solvent is isolated together with the acid anhydride which has formed, the solvent does not have to be separated when the anhydride is optionally subsequently hydrolyzed. It may be advantageous to use a solvent/anhydride mixture for hydrolysis, as the solvent acts as a dissolving intermediary between water and the anhydride which is, under certain circumstances, water-immiscible.

The process is, of course, very suitable for being continuously carried out. In this instance, diisocyanate and carboxylic acid and/or anhydride, together with water and optionally a solvent are separately or in admixture metered into the first of from 4–6 cascade-shaped mixing reactors which are connected in tandem such that there is a period of residence of from 2 to 8 hours until it leaves the last reactor. The temperature in the individual reactors may either be a uniform 100°–140° C. or rise from 60°–140° C. or preferably from 80°–120° C.

Depending on the boiling points of diisocyanate, acid anhydride which is formed and solvent which may be used, the reaction mixture is either initially passed over a continuously operating distillation column to separate the anhydride, optionally together with the solvent, and the biuret-polyisocyanate is subsequently freed of excess diisocyanate and residues of anhydride and solvent which may be present by thin-layer distillation or extraction. (This procedure may be used if the anhydride which has been formed is to be hydrolyzed to produce acid and reused). Or, alternatively, the biuret-polyisocyanate is initially freed of excess diisocyanate, anhydride and solvent by a common thin-layer evaporation and the evaporated product is subsequently separated into diisocyanate and anhydride by distillation column. The solvent, which may be used, either being separately removed or being removed together with one of the other constituents. The anhydride which is thus produced, optionally in admixture with solvent, is subsequently continuously or discontinuously, completely or partially, hydrolyzed to produce acid and then, like the excess diisocyanate, is reintroduced into the process.

During the preferred reaction of 1,6-diisocyanatohexane with water and pivalic acid, the pivalic acid anhydride which is formed is initially separated over a column and then hydrolyzed, and the biuretpolyisocyanate is subsequently freed of excess 1,6-diisocyanatohexane by thin-layer evaporation.

If, in contrast, the anhydride itself is used as a catalyst, it may be separated by thin-layer distillation, together with excess diisocyanate and solvent which may be used and the resulting mixture is then reintroduced into the process without further purification.

The polyisocyanates which have a biuret structure and are produced according to the present process are distinguishable by their good color quality and good stability in storage and are, to a large extent, free of by-products. They are very suitable for the production of light-fast lacquers which are extremely resistant to the effects of exposure and have excellent gloss life.

The present process is described in more detail with reference to the following Examples. Percentages refer to percent by weight.

EXAMPLES

EXAMPLE 1

5,040 g (30 mols) of hexamethylene diisocyanate were introduced at 90° C. into a 6 l four-necked flask having a contact thermometer, a stirrer and a reflux cooler. Over a period of 70 minutes, 73.8 g (4.1 mols) of distilled water and 183 g (1.8 mols) of melted pivalic acid were incrementally added dropwise from two separate dropping funnels with good stirring. Shortly after the beginning of this stage, a constant $CO_2$ development began: on completion of this addition 85.1 l (standard conditions) of $CO_2$ (76% of the theoretical yield) were measured using a gas meter. The solution was subsequently stirred for a further 30 minutes at 100° C. and for 60 minutes at 120° C. The production of gas was then complete 109 l (standard conditions) or (97% of the theoretical yield). The NCO- content of the clear, crude biuret solution was 37.1%. The solution was freed of small quantities of solid substance by filtration and worked up by thin-layer distillation. 205 g of a biuret-polyisocyanate were obtained which had the following properties:

NCO content: 22.5%
Viscosity at 25° C.: 7300 mPa.s
APHA color number: 20–30
Monomer content: 0.15%
After storage: 0.2%
(6 weeks, 50° C.)

The thin layer distillate (2,980 g) contained 152 g (91% of the theoretical yield) of pivalic acid anhydride according to gas chromatographical analysis. The anhydride was used in the next experiment without subsequent treatment.

EXAMPLE 2

2,980 g of the distillate from Example 1, which contained 2,828 g (16.8 mols) of hexamethylene diisocyanate and 152 g (0.82 mols) of pivalic acid anhydride were introduced together with a further 3,226 g (19.2 mols) of hexamethylene diisocyanate and 500 ml of phosphoric acid triethylester, at 120° C. Over a period of 60 minutes, 72 g (4 mols) of distilled water were added dropwise and stirred for a further 80 minutes at the same temperature. At this point, 87.6 l (standard conditions) of $CO_2$ (97.8% of the theoretical yield) were produced. At 15 mm a fraction of 200 g was distilled off via a packed column (50 cm in height 5 cm in diameter) having a reflux separator (reflux ratio about 1:1) and contained 141 g (93% of the theoretical yield) of pivalic acid anhydride and 58 g of triethyl phosphate according to GC-analysis. Only traces of hexamethylene diisocyanate were obtained. A pivalic acid solution was produced by rapid boiling with an equimolar quantity of water, which solution may be used in further mixtures.

The completely clear, crude biuret which was obtained was worked up by thin-layer distillation to produce 1,930 g of a biuret-polyisocyanate which had the following properties:

NCO content: 23.7%
Viscosity at 25° C.: 2350 mPa.s
APHA color number: 20
Monomer content: <0.1%

EXAMPLE 3

1,680 g (10 mols) of hexamethylene diisocyanate were introduced together with 100 ml of 1,4-dioxane at 100° C. and over a period of 40 minutes, a solution of 32.4 g (1.8 mols) of distilled water and 40.8 g (0.4 mols) of pivalic acid in 100 ml of dioxane were added dropwise. After a further 60 minutes, at 120° C., a clear, crude biuret solution having an NCO content of 35.2% (35.5% was calculated) was produced with the release of the calculated quantity of $CO_2$. After the solvent had been distilled off under vacuum, the product was extracted in an extraction column with n-hexane. A biuret polyisocyanate was obtained which had the following properties:

NCO content: 21.5%
Viscosity at 25° C.: 15,800 mPa.s
APHA color number: 10–20
Monomer content: 0.13%
After storage: 0.17%

(6 weeks, 50° C.)

Comparative Example I

The process was carried out as Example 3 using an equimolar quantity of formic acid instead of pivalic acid. After about half the calculated quantity of carbon dioxide had been released, the mixture began to cloud. During the course of the reaction a voluminous, flocculent precipitate of urea intermediate product was produced. After the production of gas was complete, the mixture was heated for a period of 3 hours at 142° C. (reflux of the dioxane), but the precipitate did not dissolve. No subsequent processing was carried out.

Comparative Example II

Example 3 was repeated; the same molar quantity of acetic acid was used instead of pivalic acid. There was only minimal clouding in comparison with Comparative Example I. A distinct yellowing was observed shortly after the beginning of the reaction, which became more intense towards the end of the reaction. Since the crude biuret solution had an APHA color number above 120, no processing was carried out.

Comparative Example III 1,008 g (6 mols) of hexamethylene diisocyanate, 12.75 g (0.125 mols) of acetic acid anhydride and 100 ml of 1,4-dioxane were introduced at 120° C. and mixed over a period of 40 minutes with 18 g (1 mol) of distilled water. After another hour at 120° C., the reaction was complete. Shortly after the beginning of the water addition, a distinct yellowing was observed which intensified towards the end of the reaction. Since the APHA color number of the crude solution was 180, it was not necessary to process the solution.

If in a further mixture, the quantity of acetic acid anhydride was increased to 51 g (0.5 mols) and the temperature of the water addition was lowered to 90° C., an equally strongly color crude biuret solution was obtained which was clouded by ureaprecipitates. For this reason it was unnecessary to work up the solution.

EXAMPLE 4

1,008 g (6 mols) of 3-methylpentane-1,5-diisocyanate were introduced at 90° C. and a solution of 16.2 g (0.9 mols) of distilled water and 17.2 g (0.2 mols) of methacrylic acid in 50 g of acetone were added dropwise over a period of 40 minutes. After a further 60 minutes at 110° C. the production of gas was complete (22.3 l (standard conditions) of $CO_2$ or (99.5% of the theoretical yield).

After the solvent had been drawn off under vacuum and the diisocyanate excess had been removed by thin-layer distillation, 405 g of a biuret-polyisocyanate having the following properties were obtained:
NCO content: 24.4%
Viscosity at 25° C.: 29,800 mPa.s
APHA color number: 30–40
Monomer content: 0.25%

EXAMPLE 5

1,260 g (6 mols) of trimethyl-hexane-1,6-diisocyanate (isomer mixture 2,2,4- and 2,4,4-) were mixed at 60° C. with 200 ml of 1,2-dimethoxy ethane, 8.1 g (0.45 mol) of water and 11.6 g (0.1 mol) of 2,2-dimethyl butyric acid and subsequently stirred at the same temperature. After several minutes, there was a slight production of carbon dioxide. Over the course of 5 hours, 19.6 l (standard conditions) of $CO_2$ (87.5% of the theoretical yield) were produced. At this point the mixture was clouded by flocculent precipitates. Over the course of 3 hours, the temperature was increased in stages to 140° C. The precipitate gradually dissolved and the $CO_2$ quantity increased to 22.6 l (standard conditions) (101% of the theoretical yield). A fraction of 53 g was then distilled off at 0.2 mm, which fraction contained 9.9 g (92.5% of the theoretical yield) of 2,2-dimethyl butyric acid anhydride according to gas chromotographical analysis. The crude biuret solution was subjected to thin-layer distillation (surface temperature 170° C., 0.3 mm) and produced a biuret-polyisocyanate which had the following properties:
NCO content: 18.5%
Viscosity at 25° C.: 11,300 mPa.s
APHA color number: 40
Monomer content: 0.35%

EXAMPLE 6

A mixture of 3,360 (20 mols) of hexamethylene diisocyanate, 93 g (0.5 mols) of pivalic acid anhydride and 300 g of phosphoric acid triethylester were introduced at 120° C. and over a period of 40 minutes. 36 g (2 mols) of distilled water were added dropwise. After a further two hours at 120° C. the solution was worked up by thin-layer distillation. 890 g of biuret-polyisocyanate a were obtained.

The distillate (2.803 g) was mixed with 941 g of fresh hexamethylene diisocyanate (3.744 g total) and reacted as above while 35.1 g (1.95 mols) of water and 10.2 g (0.1 mols) of pivalic acid were incrementally added dropwise from a separate dropping filter. (Biuret-polyisocyanate b). Method b was repeated a further three times (c–e). The following results are obtained:

| Biuret-polyisocyanate | a | b | c | d | e |
| --- | --- | --- | --- | --- | --- |
| Yield (g) | 890 | 887 | 885 | 885 | 880 |
| NCO content (%) | 23.9 | 23.8 | 23.8 | 23.7 | 23.7 |
| Viscosity at 25° C. (mPa·s) | 1850 | 1860 | 1860 | 1880 | 1910 |
| APHA color number | 30–40 | 30 | 20–30 | 20 | 20 |
| Monomer content (%) | 0.15 | 0.21 | 0.18 | 0.05 | 0.08 |
| Quantity of distillate | 2803 | 2800 | 2795 | 2802 | 2805 |

The distillate of the last mixture contained 290 g of phosphoric acid triethylester and 98 g pivalic acid anhydride according to gas chromatographical analysis. Therefore the losses of catalyst were less than the quantity of pivalic acid which was added to compensate for the losses.

EXAMPLE 7

33.6 kg (200 mols) of hexamethylene diisocyanate, 3 l of acetone and 744 g (4 mols) of pivalic acid anhydride were introduced into a 50 l mixing autoclave (which had a cooling bank of tubes) at 120° C. and over a period of 2 hours were mixed using a piston metering pump with 612 g (34 mols) of distilled water. A pressure valve was fixed to the top of the cooler and set at 5 bars.

After about 15 mols of water (40 minutes) had been added, the inside pressure of the vessel reached the preset 5 bars and carbon dioxide began to escape. The quantity was recorded using a gas meter. After all the water had been added, the mixture was stirred for a further 2 hours at 120° C. The quantity of $CO_2$ which was measured ( 470.4 l at standard conditions or 21 mols) increased to a final value of 76.5 l (standard conditions) or 34.2 mols after the vessel had cooled to 80° C. and the pressure was reduced to ambient pressure. The transparent, clear, crude biuret solution was freed of solvent, pivalic acid anhydride and some of the isocyanate excess using a falling film evaporator, and was subsequently distilled using a thin-layer evaporator. 14.1 kg of a biuret-polyisocyanate was obtained which had the following properties:

NCO content: 22.3%
Viscosity at 25° C.: 9,800 mPa.s
APHA color number: 20–30
Monomer mixture: 0.35%
After storage: 0.43%
(12 weeks, 50° C.)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of polyisocyanates which have a biuret structure by reacting an aliphatic diisocyanate with water at elevated temperature in the presence of
   (a) an $\alpha,\alpha,\alpha$-tri-substituted acetic acid which does not have any other isocyanate-reactive groups other than the carboxyl group,
   and/or
   (b) an anhydride of the acid mentioned in (a),
   wherein (a) is present in an amount of up to 0.39 mols per mol of water, (b) is present in an amount of up to about 2 mols per mol of water and the total quantity of (a) and (b) is at least 0.02 to about 2 mols per mol of water.

2. The process of claim 1 wherein said aliphatic diisocyanate is 1,6-diisocyanatohexane.

3. The process according to claim 1 wherein trimethyl acetic acid is used as component (a) and/or trimethyl acetic acid anhydride is used as component (b).

4. The process according to claim 2 wherein trimethyl acetic acid is used as component (a) and/or trimethyl acetic acid anhydride is used as component (b).

5. The process of claim 1 wherein said process is conducted in the presence of a water-miscible solvent.

6. The process of claim 1 which comprises removing unreacted starting diisocyanate from the polyisocyanates having a biuret structure by distillation and/or extraction.

7. A process for the production of polyisocyanates which have a biuret structure by reacting 1,6-diisocyanatohexane with water at elevated temperature in the presence of
   (a) trimethyl acetic acid and/or
   (b) trimethyl acetic acid anhydride
   wherein (a) is present in an amount of up to 0.39 mols per mol of water, (b) is present in an amount of up to about 2 mols per mol of water and the total quantity of (a) and (b) is at least 0.02 to about 2 mols per mols of water.

8. The process of claim 7 which additionally comprises removing unreacted 1,6-diisocyanatohexane from the polyisocyanates which have a biuret structure by distillation and/or extraction.

* * * * *